United States Patent [19]  [11] 4,436,937
Baardman et al.  [45] Mar. 13, 1984

[54] PROCESS FOR THE RING ALKYLATION OF AN ANILINE

[75] Inventors: Frank Baardman; Robert van Helden; Margaretha J. de Nie-Sarink, all of Amsterdam, Netherlands

[73] Assignee: Shell Oil Company, Houston, Tex.

[21] Appl. No.: 436,215

[22] Filed: Oct. 25, 1982

[30] Foreign Application Priority Data

Nov. 11, 1981 [GB] United Kingdom ............... 8133996

[51] Int. Cl.$^3$ ............................................. C07C 85/24
[52] U.S. Cl. ................................................ 564/409
[58] Field of Search ..................................... 564/409

[56] References Cited

U.S. PATENT DOCUMENTS

| | | | |
|---|---|---|---|
| 3,275,690 | 9/1966 | Stroh et al. | 260/576 |
| 3,678,113 | 7/1972 | Klopfer | 564/409 |
| 3,868,420 | 2/1975 | Evans et al. | 564/409 |
| 3,923,892 | 12/1975 | Klopfer | 260/578 |
| 4,128,582 | 12/1978 | Governale et al. | 564/409 |

FOREIGN PATENT DOCUMENTS 1051271 9/1959 Fed. Rep. of Germany ...... 564/409

OTHER PUBLICATIONS

R. Stroh et al., Angewandte Chemie, vol. 69, pp. 124–131 (1957).

*Primary Examiner*—Paul F. Shaver

[57] ABSTRACT

An aniline is alkylated on the ring by treating it with an alkylating agent, preferably an alkyl chloride, in the liquid phase, and in the presence of at least 1.02 mole of an aluminum halide per mole of the aniline.

8 Claims, No Drawings

PROCESS FOR THE RING ALKYLATION OF AN ANILINE

BACKGROUND OF THE INVENTION

It is well known that aromatic compounds can be alkylated in the aromatic nucleus by reaction with various alkylating agents in the presence of a protonic acid or a Lewis acid as catalyst. Such is known as the Friedel-Crafts reaction. A very wide range of acidic catalysts, of which aluminum chloride may be the best known example, have been used to prepare a wide variety of alkyl-substituted benzene derivatives.

Such reactions are of great importance and of wide applicability. They can, however, suffer from at least three principal limitations. First, it can be rather difficult to prevent di-alkylation of the benzene nucleus, since the first product formed, the monoalkylated product, tends to be more reactive than the starting material. Thus, it is often necessary to conduct the reaction in such a way that only a relatively small proportion of the aromatic starting material reacts, and then to separate off the product or products formed, and recycle the starting material. On an industrial scale, such procedures can be very costly.

Second, when using certain substituted benzenes as starting materials, alkyl substitution can lead to two or more positional isomers. In some cases, one isomer is formed in large excess over the other possible isomer; in many cases, however, the reaction is relatively unspecific, and mixtures of some or all of the possible isomers are formed.

Third, as is stated clearly in a well known textbook:
" . . . aromatic rings containing the —NH$_2$, —NHR, or —NR$_2$ group do not undergo Friedel-Crafts alkylation, partly because the strongly basic nitrogen ties up the Lewis acid needed for ionization of the alkyl halide:

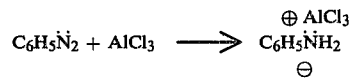

Tying up of the acidic catalyst by the basic nitrogen is not the only factor that prevents alkylation, since when excess catalyst is used, reaction does not occur". R. T. Morrison and R. N. Boyd, *Organic Chemistry*, third edition, (Boston) 1974[5], page 382, Chapter 12.8, "Limitations of Friedel-Crafts Alkylation".

Only one exception to this general rule has been discovered, in 1955, by Stroh, et al. (German Auslegeschrift No. 1,051,271; U.S. Pat. No. 3,275,690), who found that it is possible to alkylate aromatic amines using liquefied lower olefins in the presence of, e.g. aluminum chloride, at high temperatures and pressures, e.g. 300° C. and 250 atm. Under these severe conditions the aromatic nucleus is alkylated, selectively, but only at the position(s) ortho to the amino group. Only if both ortho-positions are already occupied by substituents, and then not always, para-alkylation may take place. The highest molar ratio of aluminum halide to the aniline used is 0.028.

Accordingly, the art has not provided a process suitable for the large-scale selective alkylation of aromatic amines (anilines) to 4-alkylanilines or N-alkyl congeners.

DESCRIPTION OF THE INVENTION

It now has been found that an aniline can be selectively alkylated at the para-position of the ring, relative to the amino moiety, by treating the aniline with an alkylating agent in liquid phase in the presence of at least 1.02 moles of an aluminum halide per mole of the aniline.

A considerable advantage of the present process in comparison to the known method is that the reaction does not have to be carried out at high temperatures or pressures. Preferably, the alkylation is carried out at a temperature below 150° C., more preferably at a temperature in the range from −30° C. to 40° C., especially in the range from −5° C. to 20° C., and in particular from 5° C. to 10° C. If the volatilities of the reagents at the reaction temperature chosen are such that pressure is not needed to maintain them in liquid phase, the alkylation can be carried out at atmospheric pressure.

The treatment of the aniline is carried out in the liquid phase, and either with or without a solvent. A solvent may be omitted if the reagents and the catalyst form a liquid when brought together. In most cases, however, the complex of the aniline and the aluminum halide is solid. Preferably, therefore, the alkylation is carried out in solution in a solvent.

The solvent preferably is an anhydrous, organic liquid, sufficiently polar to dissolve the aluminum halide-aniline complex, and also to dissolve a sufficient amount of the alkylating agent. Water is known to deactivate the aluminum halide catalyst. Halogenated, particularly chlorinated, lower alkanes are suitable as solvents, 1,2-dichloroethane being much preferred. In some cases, the solvent and the alkylating agent may be the same compound, especially if the present process is to be used for the preparation of polyalkylated anilines.

The catalyst used is an aluminum halide, e.g. aluminum bromide and/or aluminum chloride. Aluminum chloride is preferred, since aluminum bromide is strongly deliquescent and difficult to handle.

On contacting the aluminum halide and the aniline a 1:1 complex is formed, usually accompanied by a temperature rise. It is possible to dissolve the aniline in a suitable quantity of solvent before adding the aluminum halide, but it is equally possible to add the aniline to the aluminum halide. The presence of a solvent has the added advantage of absorbing some of the heat of reaction.

There is a distinct lower limit of 1.02 moles of aluminum halide per mole of the aniline; however, there is no distinct upper limit, except the one dictated by the solubility. Preferably from 1.05 to 2.0 moles of aluminum halide per mole of the aniline is used, in particular from 1.05 to 1.15 mole/mole, especially 1.07 mole/mole.

As alkylating agent many of the known Friedel-Crafts alkylating agents are suitable. Preferably, an alkyl halide or an alkanol is used as the alkylating agent. However, when using an alkanol it must be kept in mind that the aluminum halide will form a complex with it, so that an extra equivalent (based on the alkanol) of catalyst must be used. The water formed when using an alkanol is used as alkylating agent can have a detrimental effect on the catalyst, which may be reflected in the conversion and the selectivity levels. Therefore, alkyl halides, particularly alkyl chlorides, are preferred as alkylating agents.

Defined in general terms, the suitable alkylating agents are those wherein a halogen atom or a hydroxyl moiety is bonded to a saturated aliphatic carbon atom. That carbon atom, in turn, can otherwise be bonded to hydrogen (i.e., be a halomethyl moiety); to a carbon atom of an alkyl moiety; to a carbon atom of an alkenyl moiety (i.e., as in a haloallyl moiety); to a carbon atom of an alkynyl moiety (i.e., as in a halopropargyl moiety); or to a carbon atom of an alicyclic or aromatic ring moiety. Such moieties may be substituted. The alkyl moiety suitably is straight-chain or branched-chain in configuration. Examples include methyl, ethyl, propyl, isopropyl, butyl, isobutyl, sec.-butyl, tert.-butyl, but larger groups, e.g. squalanyl, are not excluded. Should a substituent form a complex with the aluminum halide catalyst, as is the case with the hydroxyl group, then an extra equivalent of catalyst must be allowed for this effect.

As is normal in Friedel-Crafts reactions, a group introduced into the aniline nucleus may in some cases be a different group from a group present in the alkylating agent. Usually, products in which the group that is introduced is a tertiary or secondary group rather than a primary group, predominate when the group has three or more carbon atoms. For example, an isopropyl group can be introduced by the use of either isopropyl chloride or n-propyl chloride as alkylating agent: under the reaction conditions, tthe same transient intermediate is formed and leads mainly to isopropylation of the aniline nucleus. The use of isopropyl chloride, however, causes a faster conversion.

Olefins and dialkyl ethers also may be used as alkylating agents, although their relatively lesser activity makes them less preferred.

Whatever alkylating agent is selected, it is in general preferred that the alkylating agent be added quickly, in particular all at once, to the mixture of the aniline and the aluminum halide. It appears that straight addition, in particular without added solvent, provides high conversions and high selectivities to para-substitution. The above refers, of course, to batch preparations, but it is to be understood that the present process can be carried out continuously as well. In the latter case a plug flow-type reactor is preferred, resulting in a narrow residence time distribution of the reactants, and in which the residence time can be varied according to the required product purity and yield.

Analyses of the product after regular periods of time from the start of the reaction indicate that the conversion of the aniline increases with time, but that the yield of para-substituted product decreases. To prevent further alkylation, it is advantageous if the alkylation reaction is stopped by adding a quenching agent.

Preferably, the quenching agent destroys the catalyst and/or the complex between the catalyst and the aniline: e.g., water or alcohol can be used as the quenching agent. It appears to be particularly advantageous, however, if the quenching is combined with the work-up of the product—for example, when an alkyl chloride is used as the alkylating agent, it may be desirable that the hydrogen chloride that is formed be neutralized and/or removed from the amino group of the aniline. Preferably, therefore, the quenching agent is an aqueous solution of a base, e.g. caustic soda or ammonia.

The molar ratio of the alkylating agent to the aniline preferably lies in the range of from 0.5 to 1.30, in particular from 0.8 to 1.2. It appears that at low molar ratios the conversion of the aniline is low, but that the selectivity towards para-substitution is high, whereas at higher molar ratios this situation reverses.

If the present process is applied in the preparation of polyalkylated products—including a para-alkyl group—the alkylation reaction should be allowed to proceed as long as practicable and/or necessary. The more alkylating agent is used, the more polyalkylated products will be formed.

The aniline may be any aromatic amine, including aniline itself. The amino group may be primary, secondary or tertiary—i.e., the compound may contain the —NH$_2$ group or may be an N-alkyl or N,N-dialkyl compound. The aromatic nucleus of the anilines may be substituted, except, of course, at the para-position, with one or more substituents such as halogen, nitro, nitroso, acyl, alkoxy, alkylthio, sulfono, hydroxy, cyano, and like moieties, and in particular alkyl groups. Certain substituents, however, are known to complexes with the aluminum halide, in which cases one or more extra equivalents of aluminum halide must be added to allow for this effect. Advantageously, the aniline is a nuclearly alkylated aniline. Of particular interest because of the products that can be prepared therefrom are 3-methylaniline and m-toluidine.

Under optimum conditions, conversions of about 80% and selectivities to the para-compound of 70-80% can be achieved when using m-toluidine as the aniline and isopropyl chloride as the alkylating agent. Advantageously, the alkylating agent is isopropyl chloride, if one wants to prepare 3-methyl-4-isopropylaniline—i.e., p-isopropyl-m-toluidine. This compound is an intermediate in the preparation of 1,1-dimethyl-3-(4-isopropyl-3-methylphenyl)urea, which is an extremely potent selective herbicide for the control of weeds in cereal crops. Thus, the invention also provides a process for the preparation of said urea, which process includes the step of preparing the compound 3-methyl-4-isopropylaniline by the process according to the invention. Conversion of the aniline to the urea may, for example, be carried out by reaction of the toluidine with a dimethylcarbamoyl halide, or by reaction of the toluidine with phosgene followed by reaction with dimethylamine.

EXAMPLES

The following Examples illustrate the invention. Analyses were carried out by NMR and/or gas-liquid chromatography. The results of Examples 1 to 9 are tabulated in Table I.

EXAMPLE 1

Analytical quality 97% pure aluminum chloride (13.73 g; 99.9 mmol) was added to a stirred solution of m-toluidine (10.0 g; 93.3 mmol) in dried 1,2-dichloroethane (100 ml) at room temperature, under nitrogen. The molar ratio of aluminum chloride to m-toluidine thus was to 1.07:1. The temperature rose to about 45° C. The reaction mixture was kept at this temperature, until all of the aluminum chloride had dissolved. The resulting clear, dark brown solution was cooled to 10° C. in a water bath. Then, a solution of isopropyl chloride (10.0 ml; 110 mmol) in 1,2-dichloroethane (30 ml) was added to the reaction mixture over a period of 8 minutes. The molar ratio of isopropyl chloride to m-toluidine thus was 1.18:1. The temperature temporarily rose to about 12° C. A sample, taken 2 minutes after complete addition of the isopropyl chloride, was shown to have composition 1A (Table I).

TABLE I

| | 1A | 1B | 2A | 2B | 3A | 3B | 4A | 4B | 5A | 5B | 6A | 6B | 7A | 7B | 8A | 8B | 9A | 9B |
| --- | --- | --- | --- | --- | --- | --- | --- | --- | --- | --- | --- | --- | --- | --- | --- | --- | --- | --- |
| m-toluidine | 22.6 | 18.2 | 34.3 | 16.3 | 27.7 | 14.0 | 23.1 | 15.4 | 33.0 | 28.3 | 14.8 | 10.7 | 67.6 | 33.2 | 50.0 | 48.3 | 36.3 | 27.7 |
| o-alkylated product (2-isopropyl-5-methylaniline) | 3.9 | 3.2 | 3.3 | 3.8 | 3.2 | 3.7 | 3.4 | 2.7 | 2.9 | 2.7 | 4.7 | 3.3 | 1.3 | 2.5 | 2.2 | 2.1 | 4.6 | 4.3 |
| m-alkylated product (3-isopropyl-5-methylaniline) | 4.3 | 4.4 | 3.5 | 4.6 | 4.3 | 4.7 | 4.6 | 7.4 | 3.8 | 4.7 | 5.0 | 7.1 | 2.0 | 4.2 | 3.0 | 3.2 | 4.8 | 5.7 |
| p-alkylated product (4-isopropyl-3-methylaniline) | 64.1 | 59.1 | 56.0 | 68.5 | 60.7 | 71.5 | 58.3 | 45.0 | 55.6 | 59.7 | 72.3 | 58.1 | 28.2 | 51.9 | 41.7 | 44.5 | 48.4 | 48.0 |
| dialkylated products | 4.3 | 14.5 | 1.7 | 3.6 | 0.9 | 3.1 | 6.1 | 22.8 | 1.4 | 3.5 | 2.3 | 16.5 | 0.4 | 3.9 | 1.0 | 0.5 | 4.8 | 11.0 |

Note:
all figures are GLC area percentages.

The reaction was quenched 37 minutes after complete addition of the isopropyl chloride, by the addition of 25% aqueous ammonia (45 ml). This solution was added at such a rate that the temperature of the reaction mixture was kept below about 40° C. A massive white precipitate was formed. After complete addition of the aqueous ammonia the solids were filtered off and washed with diethyl ether (100 ml). The filtrate was washed with water (50 ml) and the solvent was evaporated. The residual brown oil (14.0 g) was shown to have composition 1B (Table I).

EXAMPLE 2

The procedure of Example 1 was followed except that 13.10 g (95.3 mmol) aluminum chloride was used. The molar ratio of aluminum chloride to m-toluidine thus amounted to 1.02:1. A sample, taken 2 minutes after complete addition of the isopropyl chloride, was shown to have composition 2A. The product (13.1 g) was shown to have composition 2B.

COMPARATIVE EXAMPLE

The experiment was repeated using only 1.01 equivalents of aluminum chloride. The solution of aluminum chloride and m-toluidine was green and did not turn brown. No heat was evolved upon addition of the isopropyl chloride. No reaction occurred.

EXAMPLE 3

The procedure of Example 1 was followed except that the reaction was carried out at −5° C. A sample, taken 2 minutes after complete addition of the isopropyl chloride, was shown to have composition 3A. The product (11.7 g) was shown to have composition 3B.

EXAMPLE 4

The procedure of Example 1 was followed except that the reaction was carried out at 20° C. A sample, taken 2 minutes after complete addition of the isopropyl chloride, was shown to have composition 4A. The product (11.8 g) was shown to have composition 4B.

EXAMPLE 5

The procedure of Example 1 was followed except that 6 ml (66 mmol) of isopropyl chloride was used. The molar ratio of alkylating agent to aniline thus amounted to 0.71:1. A sample, taken 2 minutes after complete addition of the isopropyl chloride, was shown to have composition 5A. The product (13.3 g) was shown to have composition 5B.

EXAMPLE 6

The procedure of Example 1 was followed except that 10 ml isopropyl chloride was added all at once, without 30 ml dichloroethane. The temperature temporarily rose to about 16° C. A sample, taken 2 minutes after addition of the isopropyl chloride, was shown to have composition 6A. The product (14.8 g) was shown to have composition 6B.

EXAMPLE 7

The procedure of Example 1 was followed except that n-propyl chloride (10 ml; 114 mmol) was used. The temperature of the reaction mixture did not change upon addition of the alkylating agent. A sample, taken 2 minutes after complete addition of the isopropyl chloride, was shown to have composition 7A. The product was shown to have composition 7B.

EXAMPLE 8

The procedure of Example 1 was followed except that a complex of isopropyl alcohol (56 g; 93 mmol) and aluminum chloride (12.5 g of 97% purity; 91 mmol) in 1,2-dichloroethane (50 ml) was used as the alkylating agent. The temperature temporarily rose to about 15° C. A sample, taken 2 minutes after complete addition of the alkylating mixture, was shown to have composition 8A. The product (12.8 g) was shown to have composition 8B.

EXAMPLE 9

The procedure of Example 1 was followed except that dried dichloromethane (250 ml) was used as the solvent. A sample, taken 2 minutes after complete addition of the isopropyl chloride, was shown to have composition 9A. The product was shown to have composition 9B.

EXAMPLE 10

The procedure of Example 1 was followed except that aniline (8.69 g; 93 mmol) was used instead of m-toluidine. A sample, taken 2 minutes after complete addition of the isopropyl chloride, was shown to have composition 10A. The product (11.85 g) was shown to have composition 10B. Apparently, 76.2% of the aniline was converted with a selectivity of 83% towards the para-compound after a reaction time of 45 minutes.

|  | 10A | 10B |
| --- | --- | --- |
| aniline | 42.4 | 23.8 |
| o-isopropylaniline } m-isopropylaniline | 0.9 | 1.2 |
| p-isopropylaniline | 54.0 | 63.5 |
| diisopropylaniline | 2.0 | 9.4 |

EXAMPLE 11

The procedure of Example 1 was followed except that N,N-dimethyl-m-toluidine (12.62 g; 93 mmol) was used instead of m-toluidine. A sample, taken 2 minutes after complete addition of the isopropyl chloride, was shown to have composition 11A. The product obtained after a reaction time of 45 minutes was shown to have composition 11B. After 45 minutes, both the conversion and the selectivity towards para-alkylation were 87%.

|  | 11A | 11B |
| --- | --- | --- |
| unconverted product | 37.6 | 13.4 |
| o-alkylated product } m-alkylated product | 6.1 | 8.0 |
| p-alkylated product | 54.1 | 75.6 |
| dialkylated product | — | — |

EXAMPLE 12

The procedure of Example 1 was followed except that n-butyl bromide (14.95 g; 109 mmol) was used as the alkylating agent. The temperature temporarily rose to about 10.5° C. A sample, taken 2 minutes after complete addition of the alkylating agent, was shown to have composition 12A. Because of the low conversion rate, the reaction was allowed to proceed for 3 hours. The product (11.5 g) was shown to have composition 12B. The alkylated product was shown to be 3-methyl-4-sec. butylaniline.

|  | 12A | 12B |
| --- | --- | --- |
| unconverted product | 84.4 | 53.9 |
| o-alkylated product | — | 1.2 |
| m-alkylated product | — | 1.6 |
| p-alkylated product | 15.6 | 37.9 |
| dialkylated product | — | 1.6 |

EXAMPLE 13

The procedure of Example 1 was followed except that N-methylaniline was used instead of m-toluidine. A sample taken 2 minutes after complete addition of isopropyl chloride had composition 13A. The product (after 37 minutes) had composition 13B.

|  | 13A | 13B |
| --- | --- | --- |
| unconverted product | 42.0 | 18.7 |
| o-alkylated product | | |
| m-alkylated product | 1.4 | 3.3 |
| p-alkylated product | 55.7 | 75.4 |
| dialkylated product | — | — |

EXAMPLE 14

The procedure of Example 1 was followed except that 2-fluoroaniline was used instead of m-toluidine, and the reaction temperature was 50° C. After 2 minutes, 36.9% of the starting material had been converted to products, 79.4% of which consisted of 2-fluoro-4-isopropylaniline. After 37 minutes, 45.6% of the starting material had been converted to products, 70.7% of which consisted of 2-fluoro-4-isopropylaniline.

We claim:

1. A process for the alkylation of an aniline which comprises treating the aniline with an alkylating agent in the liquid phase, at a temperature in the range of from −30° C. to 40° C., in the presence of at least 1.02 mole of an aluminum halide per mole of the aniline.

2. A process as defined in claim 1 wherein the aluminum halide is aluminum chloride, and the alkylating agent is an alkyl halide.

3. A process as defined in claim 1 wherein the treatment is carried out in solution in a solvent.

4. A process as defined in claim 3 wherein the solvent is 1,2-dichloroethane.

5. A process as defined in claim 4 wherein from 1.05 to 1.15 mole of aluminum chloride per mole of the aniline is used.

6. A process as defined in claim 5 wherein the alkylating agent is an alkyl chloride.

7. A process as defined in claim 6 wherein the molar ratio of the alkylating agent to the aniline lies in the range from 0.5 to 1.3:1.

8. A process as defined in claim 7 wherein the molar ratio of the alkylating agent to the aniline lies in the range of from 0.8 to 1.2:1.

* * * * *